United States Patent
Panin et al.

(10) Patent No.: US 9,645,261 B2
(45) Date of Patent: May 9, 2017

(54) NORMALIZATION COEFFICIENTS IN PET CONTINUOUS BED MOTION ACQUISITION

(71) Applicants: Vladimir Y. Panin, Knoxville, TN (US); Michael E. Casey, Louisville, TN (US)

(72) Inventors: Vladimir Y. Panin, Knoxville, TN (US); Michael E. Casey, Louisville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1020 days.

(21) Appl. No.: 13/739,458

(22) Filed: Jan. 11, 2013

(65) Prior Publication Data

US 2014/0200848 A1    Jul. 17, 2014

(51) Int. Cl.
*G01T 1/29* (2006.01)
*A61B 6/03* (2006.01)

(52) U.S. Cl.
CPC ............ *G01T 1/2985* (2013.01); *A61B 6/037* (2013.01)

(58) Field of Classification Search
USPC ........................................................ 702/179
See application file for complete search history.

(56) References Cited

U.S. PATENT DOCUMENTS

| | | | |
|---|---|---|---|
| 9,155,514 B2 * | 10/2015 | Panin | A61B 6/5235 |
| 2003/0178559 A1 * | 9/2003 | Hamill | G01T 1/1644 |
| | | | 250/252.1 |
| 2011/0079722 A1 * | 4/2011 | Gagnon | G01T 1/2985 |
| | | | 250/362 |

OTHER PUBLICATIONS

Gerd Muehllehner, Positron emission tomography, Published Jun. 20, 2006, Phys. Med. Biol. 51 (2006) R117-R137, Department of Radiology, University of Pennsylvania, 3400 Spruce Street, Philadelphia, PA 19104, USA.*
M. Dahlbom et al., "Implementation of True Continuous Bed Motion in 2-D and 3-D Whole-Body PET Scanning," IEEE Trans. Nucl. Sci. 48, pp. 1465-1469, 2001.
M.E. Casey et al.,"A component based method for normalization in volumePET," In: Proceedings of the 3rd International Meeting on Fully Three-Dimensional Image Reconstruction in Radiology and Nuclear Medicine, Aix-les-Bains, France, pp. 67-71, 1995.
V.Y. Panin, "Iterative algorithms for variance reduction on compressed sinogram random coincidences in PET," 2008 IEEE Nucl. Sci. Symp. and Med. Imag. Conf., pp. 3719-3725, Dresden, Germany.

* cited by examiner

*Primary Examiner* — Tung Lau

(57) ABSTRACT

Normalization coefficients in are computed for positron emission tomography (PET) continuous bed motion acquisition (CBM). The normalization coefficients for the lines-of-response in CBM account for the change in decay of the injected isotope over time and/or changes in velocity of the bed motion.

9 Claims, 3 Drawing Sheets

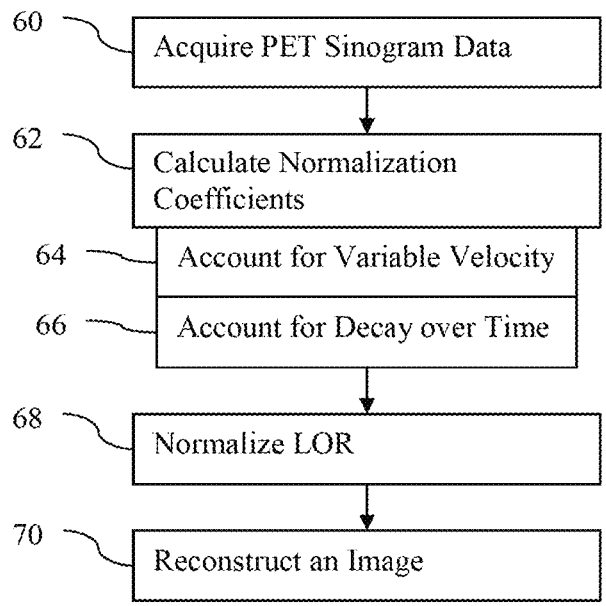
FIG. 3
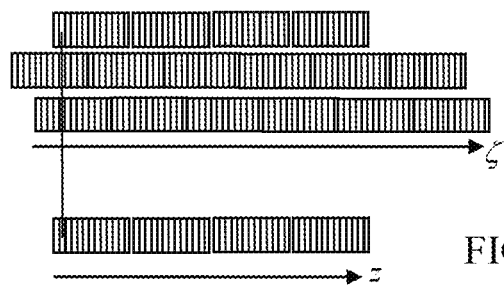
FIG. 4
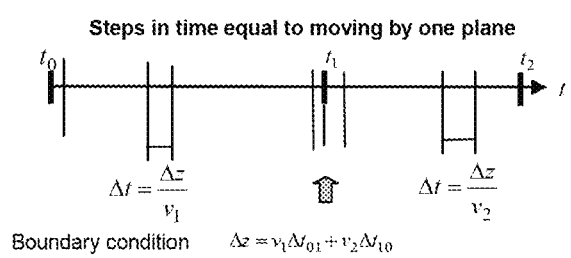

NORMALIZATION COEFFICIENTS IN PET CONTINUOUS BED MOTION ACQUISITION

BACKGROUND

The present embodiments relate to positron emission tomography (PET).

PET systems and corresponding detectors have a limited field of view. Typically, the entire patient cannot be scanned with the patient in one position. In a step and shoot (S&S) approach to scan a greater portion of the patient, the patient is moved between sequential scans, but remains stationary for each of the scans. However, the gaps between blocks of detectors cause a drop in axial sensitivity when assembling the different scans for segment zero (2D) acquisitions. For three-dimensional (3D) acquisition, greater axial uniformity may be provided for S&S. Low sensitivity spots of various segments are mixed in image space, and therefore the loss of sensitivity only occurs in the end planes.

Continuous bed motion (CBM) acquisition performs a scan of the patient while the patient is moving through the PET system. CBM may improve the axial uniformity of PET images over S&S for 2D acquisitions. For 3D acquisitions, CBM acquisition may result in super-resolution images by oversampling the image in the axial direction.

Normalization may be incomplete for CBM. The PET model represents data as a line integral (Rf) of object activity, corrected for detection efficiency:

$$\overline{p}_{i,t} = \frac{1}{n_i} \Re f_i = \frac{1}{n_i} \sum_j C_{ij,t} f_j \qquad (1)$$

where C is the system matrix with the spatial projection index i and TOF bin index t, f is the object emission activity image, identified at image voxel with index j, and n is a normalization coefficient, which represents the inverse of efficiency for a given detector pair. The detector pair defines the line of response (LOR). In the current clinical S&S mode, the normalization coefficient is decomposed into the geometrical component, crystal efficiencies, and sinogram plane efficiencies. Crystal efficiencies are corrected for dead time when the singles rate per detector is known. Decay correction, an activity efficiency factor, is applied in the image domain in S&S reconstruction, outside of the normalization coefficients. In S&S, the normalization coefficients may be computed as in any PET scan. For CBM, the continuous motion of the patient may result in inaccuracies in the PET model for the normalization coefficient.

BRIEF SUMMARY

By way of introduction, the preferred embodiments described below include methods, systems, and non-transitory computer readable media for computing normalization coefficients in continuous bed motion acquisition (CBM). The normalization coefficients for the lines-of-response in CBM account for the change in decay of the injected isotope over time and/or changes in velocity of the bed motion.

In a first aspect, a method is provided for computing normalization coefficients in continuous bed motion acquisition. A positron emission tomography (PET) scanner with a plurality of rings of detectors acquires line-of-response events from radioactive decay of an isotope in a patient while the patient is moving at different velocities in the PET scanner. Normalization coefficients are calculated for the line-of-response events. The normalization coefficients are a function of a decay correction efficiency for the isotope and step sizes that vary as a function of time in response to the different velocities. The line-of-response events are normalized with the normalization coefficients. An image of the patient is reconstructed with an output of the normalizing.

In a second aspect, a non-transitory computer readable storage medium has stored therein data representing instructions executable by a programmed processor for computing normalization coefficients in continuous bed motion acquisition. The storage medium includes instructions for calculating a continuous bed motion normalization coefficient as a function of a scanner normalization coefficient, variable bed speed, and a difference in time of acquisition of sinogram segments, and normalizing line-of-response data as a function of the continuous bed motion normalization coefficient.

In a third aspect, a system is provided for computing normalization coefficients in continuous bed motion acquisition. A bed is configured to move during a positron emission tomography (PET) scan. Axial spaced rings of detectors are operable to perform the PET scan while the bed moves. A processor connects to the detectors. The processor is configured to determine normalization coefficients as a function of a decay correction efficiency for an isotope used during the PET scan, and the processor configured to weight line-of-response data as a function of the normalization coefficients.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 3 is a flow chart of an embodiment of a method for computing normalization coefficients in continuous bed motion acquisition;

FIG. 4 illustrates accounting for variable bed velocity for computing normalization coefficients in continuous bed motion acquisition.

DETAILED DESCRIPTION OF THE DRAWINGS AND PRESENTLY PREFERRED EMBODIMENTS

Normalization coefficients are computed for positron emission tomography (PET) continuous bed motion (CBM) acquisition where the speed of the bed may vary. The CBM normalization coefficients are a combination of standard scanner normalization coefficients, but also take into account one or more other terms. The decay over time, dead time, variable bed speed, and difference in time of acquisition for various sinogram segments are accounted for in CBM normalization.

PET measures the activity for each ring of detectors. For CBM, a given line-of-response uses different detector pairs while the patient moves through the PET scanner. To normalize or scale each line-of-response for the corresponding detector pairs, the efficiency of the detector for the given detectors is estimated. By normalizing based on this efficiency, a more accurate measure of activity may result.

Figure 1:
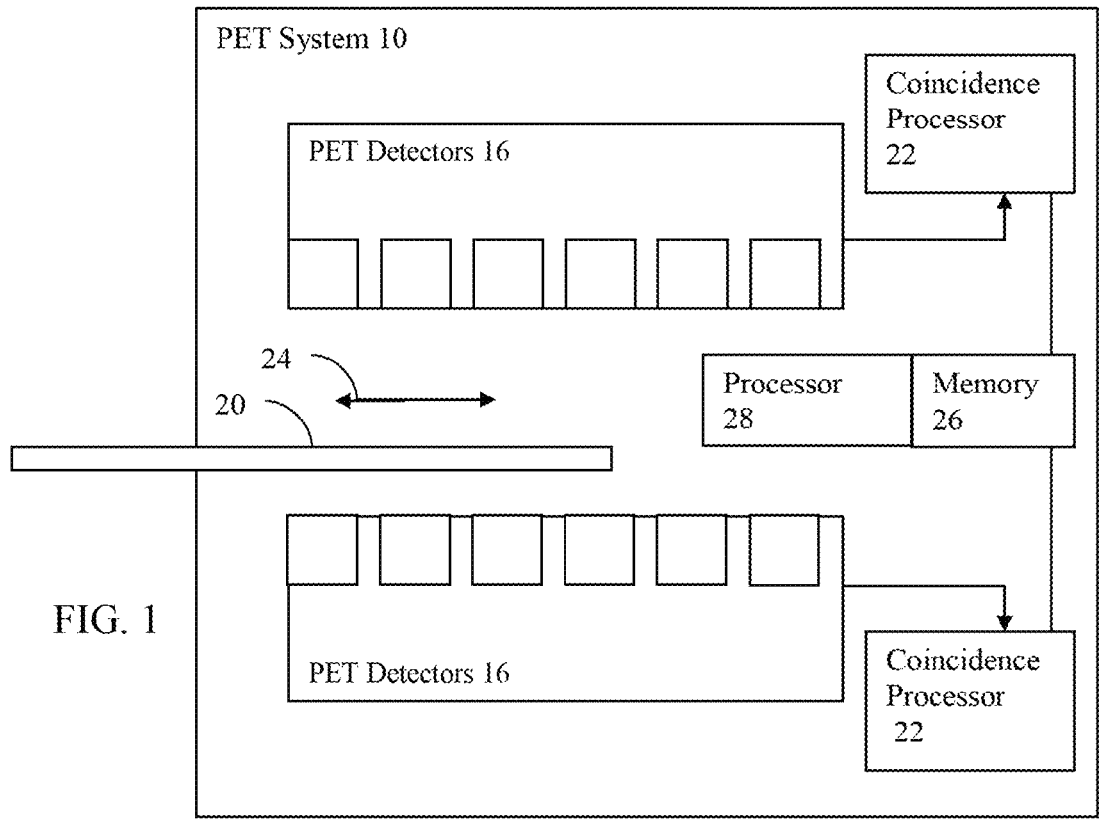
FIG. 1 is a block diagram of a system, according to one embodiment, for computing normalization coefficients in continuous bed motion acquisition.

FIG. 1 shows a PET system 10 for computing normalization coefficients in continuous bed motion acquisition. The PET system 10 includes rings of detectors 16, a bed 20, coincidence processors 22, a memory 26, and a processor 28. The processor 28, memory 26, and/or a display are part of the PET system 10 or are separate (e.g., a computer or workstation). Additional, different, or fewer components may be provided. For example, the system is a computer without the detectors 16 and bed 20, instead relying on data acquired by a separate scanner. As another example, the PET system 10 includes power supplies, communications systems, and user interface systems.

The bed 20 is a gurney, table, or other support to hold an examination subject such as a patient. A robot, gears, cable, track, and/or other device moves the bed 20. The movement is along an axial dimension represented by double arrow 24. The detectors 16 and/or PET scanner 10 form a bore or hollow cylinder through which the bed 20 moves the patient. The distance from the axial axis is the radial distance. The angle about the axial axis is the azimuth. Other coordinate systems, such as a cylindrical or polar coordinate system, may be used.

The movement is continuous, at least during part of the scanning. The bed 20, while supporting the patient, is moved at a same or a varying velocity along the axial dimension 24. For example, the head of the patient is scanned with 1.5 mm/s movement of the patient, and the torso is scanned with 1.0 mm/s movement of the patient. Other combinations of the same or different rates, with or without a greater number of different velocities, may be used. The movement may pass the patient through the bore or merely partly into the bore. The movement is with or without acceleration. In one embodiment, the movement is back and forth, scanning the patient multiple times in a cyclical pattern. A single pass may be used in other embodiments.

The movement occurs during scanning (e.g., detection or measurement) by the detectors 16. The PET detectors 16 are crystals or other photon detectors. For example, the detectors 16 are scintillation crystals coupled to avalanche photo diodes. In other embodiments, scintillation crystals are coupled with photomultiplier tubes. The scintillation crystals are bismuth germanium oxide, gadolinium oxyorthosilicate, or lutetium oxyorthosilicate crystals, but other crystals may be used.

Figure 2:
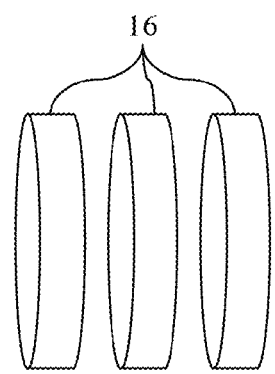
FIG. 2 shows example rings of detectors.

The detectors 16 are arranged individually or in groups. Blocks or groups of detectors 16 are arranged in any pattern around the bore. FIG. 2 represents blocks of detectors 16 arranged as separate rings around the bore. The rings are shown spaced apart, but are placed adjacent or abutting each other. Any gap may be provided between blocks within a ring, detectors within a block, and/or between rings. Any number of detectors in a block (e.g., 8 or 16), detector blocks in a ring, and/or rings may be used. The separate detectors 16 of each ring have their own singles rate and/or efficiency. The rings may extend completely or only partially around the bore.

The PET system 10 is a nuclear imaging system. The detectors 16 detect gamma rays emitted indirectly by a positron-emitting tracer. Pairs of gamma rays generated by a same positron may be detected using the ring of the detectors 16. The pairs of gamma rays travel about 180 degrees apart. If the direction of travel intersects the arrangement of detectors 16 at two locations, a coincident pair may be detected. To distinguish specific pairs, the coincidence of detected gamma rays is determined. The timing of receipt is used to pair the detected gamma rays.

As the bed 20 moves, the patient passes through the rings. A given part (e.g., organ) of the patient is within different rings at different times due to the continuous bed motion. The line-of-responses for the same part of the patient and corresponding actual three-dimensional location (i.e., point along the line-of-response) is at different locations at different times. The detectors 16 continue to detect gamma rays as the bed 20 and patient moves so different lines-of-response may be for the part of the patient at different positions within the bore.

Each individual detection output from the detectors 16 includes energy, position, and timing information. Alternatively, the detectors 16 output energy information and a receiving processor determines the timing and position (e.g., based on port assignment or connections). The timing information is used to determine coincidence of detection by different detectors by the coincidence processors 22. Pairs of gamma rays associated with a same positron emission are determined. Based on the detected event, a line-of-response is determined given the detectors involved in the detection of that event.

The detected events are passed to the memory 26 and/or processor 28. Alternatively, the coincidence processor 22 implements the computation of normalization coefficients rather than a separate processor 28. The processor 28 connects with the detectors 16, such as through the coincidence processors 22.

The processor 28 is a general processor, digital signal processor, graphics processing unit, application specific integrated circuit, field programmable gate array, digital circuit, analog circuit, combinations thereof, or other now known or later developed device for processing detected line-of-response events, computing normalization coefficients, normalizing, and/or reconstructing. The processor 28 is a single device, a plurality of devices, or a network. For more than one device, parallel or sequential division of processing may be used. Different devices making up the processor 20 may perform different functions, such as one processor for calculating normalization coefficients and another processor for normalizing the line-of-response data. In one embodiment, the processor 28 is a control processor or other processor of the PET system 10. In other embodiments, the processor 28 is part of a separate workstation or computer.

The processor 28 operates pursuant to stored instructions to perform various acts described herein, such as determining decay correction efficiency, determining a singles rate for a given time, determining detection time efficiency, calculating the normalization coefficients, normalizing the line-of-response data, and/or reconstruction. The processor 28 is configured by software and/or hardware to perform any or all of the acts of FIG. 3.

The operation and configuration of the processor 28 is first described in general below. One example implementation is described in more detail in the following discussion of FIG. 3.

The processor 28 is configured to determine normalization coefficients. The weighting to account for differences in efficiency for detecting different lines of response relative to the patient is calculated. In CBM, the lines-of-response change axial position over time when considered relative to the patient. As a result, various detector pairs and other factors contribute to the efficiency of detection. These factors, which may vary over time, are included in the computation of the normalization coefficients.

The processor 28 accounts for the decay. A decay correction efficiency is determined for an isotope used during the PET scan. The isotope's decay characteristic changes over time. This variation in decay is used for the decay correction efficiency.

The processor 28 accounts for the velocity variation of the bed and patient. As the velocity of the bed changes, the detection time efficiency changes. The detection time efficiency at different times and corresponding positions of the bed or patient during the PET scan is determined based, in part, on the velocity.

The processor 28 may account for other factors as well, such as the time variation of the singles rate and/or normalization of the scanner (e.g., normalization used in S&S or other scanning protocols without bed motion during the scan). In one embodiment, the processor 28 determines the normalization coefficients as $n^{CBM}$ at the time t:

$$1/n^{CBM} = (e^{-\lambda t} \Delta t)/(n^{scanner}(s(t))) \qquad (2)$$

where $\lambda \Delta t$ is less than 1 by at least one order of magnitude, $\lambda$ is a decay correction constant, t is time, $e^{-\lambda t}$ is the decay correction efficiency, s(t) is an empirical or estimated global singles rate of the PET detectors, $\Delta t$ is a step size (e.g., detection time efficiency), which is a function of a variable bed speed, and $n^{scanner}$ is the normalization coefficient of the detectors. $n^{scanner}$ is computed by any now known or later developed methods. The normalization calculating is integrated over time of $1/n^{CBM}$ (t).

The processor 28 applies the normalization coefficients. For each given line-of-response, the activity is weighted by the normalization coefficient for that line-of-response. The processor 28 or another processor may reconstruct the object space from the normalized lines-of-response.

The processor 28 uses the events (e.g., line-of-response events), empirical information (e.g., global singles rate), and/or known information (e.g., decay correction constant) stored in the memory 26 for processing. For processing, the data bypasses the memory 26, is temporarily stored in the memory 26, or is loaded from the memory 26.

The detected events, line-of-response information (e.g., sinograms), time step, singles rate, decay information, scanner normalization information, CBM normalization coefficients, reconstructed image, or other data is stored in the memory 26. The data is stored in any format. The memory 26 is a buffer, cache, RAM, removable media, hard drive, magnetic, optical, database, or other now known or later developed memory. The memory 26 is a single device or group of two or more devices. The memory 26 is part of the PET system 10 or a remote workstation or database, such as a PACS memory.

The memory 26 is additionally or alternatively a non-transitory computer readable storage medium with processing instructions. The memory 26 stores data representing instructions executable by the programmed processor 28 for computing normalization coefficients in continuous bed motion acquisition. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The PET system 10 may include a display. For example, the processor 28 reconstructs the patient or object being scanned from the normalized line-of-response data. The reconstruction is used for three-dimensional rendering, multi-planar reconstruction, or two-dimensional imaging of the function of the object or patient. The images are displayed on the display. The display is a CRT, LCD, plasma screen, projector, printer, or other output device for showing an image.

FIG. 3 shows a method for computing normalization coefficients in continuous bed motion acquisition. The method of FIG. 3 is implemented by the processor 28, the PET system 10, or other component or system. Additional, different, or fewer acts may be performed. For example, act 64 is provided without act 66, or vice versa. The acts are performed in the order shown or a different order.

In act 60, PET sinogram data is acquired. The acquisition is by scanning with the PET system. In alternative embodiments, the acquisition is by transfer or upload from a memory.

Line-of-response events from a patient are detected while the patient is moving in the PET scanner. The acquisition occurs over any period. For example, the acquisition is over 1, 10, 100, or other number of minutes.

The bed is moving the patient during that time. The movement is over any range of motion, such as for scanning all or only a part of the patient. The bed may move cyclically during the period, such as moving back and fourth once, five times, ten times, twenty times, forty times, or other number of times. Alternatively, the bed moves in one direction only during the scan.

The motion of the bed is continuous over at least a portion of the acquisition period. Continuous is used in the sense of motion occurring during the scanning. The continuous motion may cease or have different velocities for a part of the scanning. With cyclical motion, there may be one or more times of no motion and parts of the period with acceleration or deceleration. In alternative embodiments, a constant velocity is provided.

During the continuous bed motion, gamma rays are detected by one or more rings of detectors or other grouping of detectors. The patient ingests or is injected with a radiopharmaceutical. The radiopharmaceutical includes an isotope. The isotope decays over time, resulting in generation of a positron. The decay characteristics may change over time, such as being different for different times and corresponding bed velocities during the CBM acquisition.

Where each ring is formed from a block of X detectors along the axial direction, X planes are defined. For example, each block includes 16 detectors, so 16 planes are provided for each block. Where there are 50 rings, 530 planes are defined. The same detectors are used to detect positron-electron annihilations from different parts of the patient. Due to the motion, annihilations in a same part of the patient may be detected at different rings at different times even where the line of gamma ray propagation is the same relative to the patient for each time. Of course, the line of propagation may be different at different times for a same location of the patient.

For axial sampling, reconstruction time requirements may dictate the same CBM axial sampling (e.g., about 2 mm due to crystal pixel size) as in S&S acquisition. Other axial sampling may be used. Due to the motion of the bed during acquisition, a CBM acquisition leads to additional axial blurring. A small (i.e. smaller than an image pixel) object is effectively distributed across the whole pixel due to motion instead of staying at the pixel center, for example. On the other hand, finer (e.g., significantly less than 2 mm) CBM sampling may lead to potentially better axial resolution compared to S&S due to oversampling. Where the detector response width is significantly large as compared to the axial pixel size, less improvement may occur from oversampling. Table I provides a Fourier rebinning filtered back projection (FORE+FBP) resolution assessment of about a 0.1 mm size F-18 point source acquired with 1 mm/s bed speed. Table 1 shows full width at half maximum (FWHM) in mm of a point source with varying CBM axial sampling.

|  | CBM, 2 mm | CBM, 0.5 mm | S&S, 2 mm |
|---|---|---|---|
| Radial | 4.41 | 4.34 | 4.36 |
| Tangential | 4.36 | 4.35 | 4.36 |
| Axial | 4.95 | 4.21 | 4.51 |

The transverse resolution may not degrade in the CBM acquisition, proving that the bed movement vector is aligned with the axial scanner axis. To compare resolution measurements, the data is normalized. In CBM, the oblique segment has lower weight when comparing to S&S due to less scanning time. Normalization-free FORE+FBP reconstruction produces results biased toward segment zero resolution in CBM data, where there is no axial FORE interpolation. The non-normalized bias toward segment zero of FORE+FBP reconstruction may result in better axial resolution, which may partially offset the loss of axial resolution in CBM due to the bed motion.

The scanning with continuous bed motion acquires detected emission events for functional information. The detected gamma rays are checked for coincidence to define lines-of-response. Any time window may be used for coincidence processing, such as 0.2 microsecond coincidence time window. Each detected emission event corresponds to a line or part of a line through a patient. By detecting emission events from different angles around a patient, a volume may be reconstructed.

In act 62, the normalization coefficients are calculated. A normalization coefficient is calculated for each virtual line of response. Since the lines of response may occur along different detector pairs over time due to the patient motion, the normalization coefficient for each line of response accounts for the efficiencies of the different detector pairs. In the case of time varying effects, each virtual line-of-response has a normalization coefficient. The size of the normalization array will be the size of a non-TOF sinogram. The normalization coefficients for continuous bed motion are determined.

The normalization coefficients for each line-of-response at different positions relative to the PET scanner are calculated. The lines-of-response are at different positions relative to the patient due to different activity caused by the isotope in the patient. As the patient moves, each given line-of-response has different positions relative to the PET scanner. To account for the different detector pairs for a same line-of-response relative to the patient, the efficiencies from the different detector pairs and times of acquisition are averaged. The efficiencies corresponding to different scanner planes (e.g., detector rings or planes) are averaged, combined, or treated as the same.

Projection data are often combined in practice over a line-of-response (LOR) set, I. One example is axial spanning when various projection data are summed in the axial sinogram direction. In combining projections, the line integral through object Rf is assumed to be the same. Since PET data are of Poisson nature, modeling a combination of projection data is a summation of their means. The mean value of the combined data is:

$$\bar{p}_{I,t} = \sum_{i \in I} \frac{1}{n_i} \Re f_I = \Re f_I \sum_{i \in I} \frac{1}{n_i} \quad (3)$$

From this, efficiency of combined data (i.e. virtual LOR) is computed as:

$$\frac{1}{n_I} = \sum_{i \in I} \frac{1}{n_i} \quad (4)$$

CBM acquisition is another of example of grouping data of the same line integral together. An object's virtual lines-of-response with the same activity line integral travel across the scanner in the axial direction, encountering various detector pairs with various spatial detection efficiencies. A similar grouping of data occurs.

The normalization coefficient for each line-of-response includes terms, factors, variables, or functions accounting for the CBM. Any one or more considerations may be included. For example, one or more of detection time efficiency, decay correction efficiency, crystal efficiency (e.g., singles rate and/or dead time), or other scanner normalization terms (e.g., geometrical component and/or sinogram plane efficiencies) are accounted for in the CBM normalization coefficients. Additional, different, or fewer components of the normalization coefficients may be used.

Since the lines-of-response are acquired over time in response to variation in patient position and/or dwell time for any given detector pair, the normalization coefficient includes at least one component that is a factor of time. Where the continuous bed motion varies in velocity, at least one component accounts for the variation.

In act 64, the calculation of the normalization coefficient is a function of the detector time efficiency. The detector time efficiency represents how long a virtual line-of-response stayed in a scanner plane. The detector time efficiency accounts for different velocities. The virtual line-of-response spends different amounts of time in various detector pairs. A time step is determined. Any function may be used for the detector time efficiency.

In one embodiment, the time step corresponds to the plane separation across planes or segments. The PET scanner is separable into different segments or planes. The change in time or amount of time to transition from one plane to another at a velocity of the bed is calculated. The scanner line-of-response separation of a PET scanner (e.g., plane distance) divided by a velocity of the bed at an axial position for the time step is calculated.

With a variable bed speed, a difference in time for acquiring sinogram segments for given detector pairs results. The time step accordingly varies as well. The step size varies as a function of time in response to the different velocities of the bed and patient.

Different scans may have different protocols for bed motion. As a result, different scans have different time steps and corresponding normalization coefficients. The different combinations of step sizes result in different normalization coefficients for different patients. The normalization coefficient calculation may be different for different scans and/or patients.

To calculate the normalization, the bed movement is simulated in time and the normalization coefficients computed on-the-fly, such as calculating during an examination of a given patient before or during the scanning. The coefficients may be calculated after the examination or scanning.

One embodiment of the simulation is depicted in FIG. 4. The CBM sinogram has a transaxial index $(\rho,\theta)$ and axial index $\zeta$. The transaxial index includes both the radial coordinate $\rho$ and the polar angle $\theta$. The CBM normalization computing simulates bed movement in time step, $\Delta t$. This step is equal to the travel of the bed from one scanner line-of-response to another adjacent line-of-response or between planes of the PET scanner. During the period of the time step, the CBM sinogram planes are assumed to be aligned with scanner planes, and there is a one-to-one correspondence of scanner lines-of-response with the axial index $\zeta$ (also referred to as z) and the CBM virtual line of response (see the vertical line connecting the actual detector array along the axial direction with the three example offset detector arrays simulating different amounts of movement of the patient above).

The bed velocity may change. The computing of CBM normalization is performed with the motion represented as a piece-wise constant bed velocity. The set of velocities for this piece-wise function is given by:

$$v=\{v_0, v_1, \ldots, v_{I-1}\}. \quad (5)$$

The velocity is changed at time points $t=\{t_0, t_1, \ldots, t_I\}$. $t_0$ denotes a start of the acquisition process and $t_I$ is the time when the acquisition is stopped.

Each simulation time step is velocity dependent and corresponds to a bed movement by one plane separation. The time step and corresponding detection time efficiency is calculated as:

$$v_i \Delta t_i = \Delta z \quad (6)$$

where $\Delta z$ is the spatial scanner plane separation. The plane separation is known from the scanner, but the velocity is given by the scanning protocol. FIG. 4 shows two different values of $\Delta t$ represented as widths between two lines. Since two different velocities are used in the example of FIG. 4, the widths of the time steps are different for different times.

The border time points, when the bed velocity changes, are handled in the model. There are two time steps of interest for each velocity transition. Due to different velocities, the time steps are smaller compared to the typical step size inside the constant velocity time interval. Together, these two time steps accommodate a full plane shift:

$$v_{i-1}\Delta t_{i-1,end} + v_i \Delta t_{i,start} = \Delta z \text{ around time } t_i. \quad (7)$$

The very first and the very last time steps are also considered. The first and last time steps are not equal to the regular steps over time. The handling of the first time step depends on the hardware rebinner bed position assignment convention. At time zero, the CBM sinogram array may be aligned with the scanner so that the center of the sinogram bin coincides with the center of the detector bin. During bed movement, the very first CBM sinogram array plane center travels only half of $\Delta z$. The next time step trace progresses as the plane center travels from one edge of the scanner plane to another. The difference may be negligible due to initial alignment assumption, since the difference affects mostly the ramp up and ramp down period. Thus, the initial and final time steps are not modeled as boundary conditions. In other embodiments, the model accounts for the initial and final time steps being different form other time steps, and/or different alignments are used.

The normalization coefficients may account for the singles rate. The dead-time correction is updated over time, since the singles rate is constantly changing. The time dependency of the scanner efficiency is due to the dead-time component. The singles rate is changing due to a difference in the object region seen by the scanner.

The singles rate function is empirically determined for the scanner. The singles rate may be measured as part of calibration, at manufacture, or at another time. The singles rate may be estimated from other measurements. Since the singles rate may vary by patient, estimation based on measurements for the patient may be used.

Figure 5A:
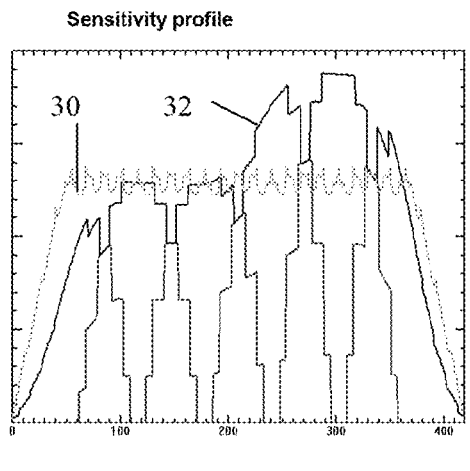
FIG. 5A shows example sensitivity profiles.

The singles rate is a relatively smooth function of time. FIG. 5D shows example singles functions over time. The changes of singles rate for four buckets, aligned transaxially, are shown. The singles rates may be filtered or smoothed or a curve fit to the singles rate. In one embodiment, the singles rate is sampled coarsely and interpolation is used to create the smoothly varying representation of the singles rate over time. Alternatively, fine sampling may be used.

The singles rate function over time is stored for use in normalization. Rather than store the entire function, the singles function may be coarsely sampled, such as a one detector block axial size sampling (e.g., a 50 mm bed axial shift). Since the CBM normalization is computed in simulation over time, the coarsely sampled axial shift is converted into corresponding time points. The singles are interpolated and obtained as a function of time. Since the expansion of scanner efficiency for a given singles rate is an expensive task, the scanner efficiency is assumed to be a smooth function of time. Linear interpolation is used to obtain the value of scanner efficiency at given time point:

$$\varepsilon_{scanner}(\rho, \theta, z, t_a \leq t \leq t_b) = \frac{t_b - t}{t_b - t_a} \varepsilon_{scanner}(\rho, \theta, z, t_a) + \frac{t - t_a}{t_b - t_a} \varepsilon_{scanner}(\rho, \theta, z, t_b) \quad (8)$$

Alternatively, fine sampling may be used.

The CBM normalization coefficients may account for the scanner normalization coefficients. The geometrical component of efficiency for the scanner is included in the normalization coefficient for the scanner. Any now known or later used normalization coefficients for measurement of a non-moving patient may be used. The scanner normalization coefficients may be measured as part of calibration, at manufacture, or at another time. The scanner normalization coefficients may be estimated from other measurements. In one embodiment, the scanner normalization coefficients are included in the detector time efficiency, singles rate efficiency, or not separately provided.

The CBM normalization coefficients may account for decay correction. The decay characteristics are specific to the type of isotope used for the PET scan. Each isotope has a decay correction constant, $\lambda$. The decay correction constant of the isotope used for a given scan is determined, such as loading from memory.

The decay correction efficiency of the isotope is included in the CBM normalization coefficients. Any model of the decay correction efficiency may be used. For example, the decay correction efficiency is modeled as an exponential factor, with the decay correction constant being an exponential term.

The activity decays during movement. The decay correction efficiency varies (e.g., decreases) over time. Since the CBM acquisition occurs over time, the activity of the radiopharmaceutical varies. Time is included in the decay correction efficiency. The exponential factor represents the decay correction efficiency at a given point relative to the scanning start point. One example function for the decay correction efficiency is $e^{-\lambda t}$, but others may be used.

The various components of the CBM normalization coefficient are combined. The combination models the efficiency as a function of time and velocity, so is a model based on the bed and patient movement through the PET scanner.

Any function may be used. In one embodiment, the continuous bed motion normalization coefficient, $n^{CBM}$, is calculated as:

$$1/n^{CBM} += (e^{-\lambda t}\Delta t)/(n^{scanner}(s(t))) \qquad (9)$$

where $\lambda t$ is less than 1 (e.g., less by an order of magnitude), $\lambda$ is a decay correction constant, t is time, $e^{-\lambda t}$ is the decay correction efficiency, s(t) is an empirical global singles rate of the PET scanner, $\Delta t$ is the step size, which is a function of the variable bed speed and the difference in time of the sinogram segments, and $n^{scanner}$ is the scanner normalization coefficient/scanner efficiency. The normalization calculating is an integration over time of $1/n^{CBM}$ (t).

Equation (9) may be expressed in terms of efficiency where the efficiency is 1/n. This may avoid the +=procedure. At a given time step, each element of CBM efficiency (i.e., reciprocal of the normalization coefficient) array is updated according to:

$$\epsilon_{\rho\theta\zeta}^{CBM}(t) = \epsilon_{\rho\theta\zeta}^{CBM}(t-\Delta t) + \epsilon_{\rho\theta z}^{scanner}(s(t))e^{-\lambda t}\Delta t,$$
$$\lambda \Delta t \ll 1$$

$$\epsilon_{\rho\theta\zeta}^{CBM}(0) = (0) \qquad (10)$$

where the scanner efficiency is computed for given single rates s. Equation (10) represents discrete approximation of the following integral with time step $\Delta t$:

$$\frac{1}{n_{\rho\theta\zeta}^{CBM}} = \int_{T_1}^{T_2} dt \frac{e^{-\lambda t}}{n_{\rho\theta z(t)}^{scanner}}, \qquad (11)$$

$$T_1 = \max(0, t_1(\zeta)), \quad T_2 = \min(T, t_2(\zeta))$$

$$z(t_1(\zeta)) = 0,$$

$$z(t_2(\zeta)) = l \text{ arg est axial index of segment}$$

where CBM normalization is over acquisition time T.

Ignoring the border effect for the detection time efficiency for simplicity, the CBM efficiency computing for a particular segment pane or axial index $\zeta$ is represented as:

$$\epsilon_{CBM}(\rho, \theta, \zeta) = \qquad (12)$$

$$\sum_{i=0}^{I-1} \sum_{j=0}^{N_i-1} \epsilon_{scanner}(\rho, \theta, \zeta - \Delta\zeta_{i,j}, t_{i,j})e^{-\lambda t_{i,j}}\Delta t_i t_{i,j} =$$

$$\sum_{i'=0}^{i-1} \sum_{j'=0}^{N_i^f-1} \Delta t_{i'} + \sum_{j'=0}^{j} \Delta t_i \Delta\zeta_{i,j} =$$

$$\sum_{i'=0}^{i-1} \sum_{j'=0}^{N_i^f-1} \Delta z + \sum_{j'=0}^{j} \Delta z \epsilon(\rho, \theta, \zeta) =$$

$$\begin{cases} \epsilon_{scanner}(\rho, \theta, \zeta), & 0 \leq \zeta < Z_{segment} \\ 0, & \text{otherwise} \end{cases}$$

where index j represents the number of time steps for bed velocity $v_i$. j steps are simulated from the moment when the bed speed is changed.

Other functions may be used for the normalization coefficient computations. Additional, different, or fewer efficiencies may be included. One or more components may be a function of time or simplified to not be a function of time. Similarly, one or more components may be a function of velocity or change of velocity or simplified to not be a function of velocity or change of velocity.

The normalization coefficients are computed as efficiency and inverted. Alternatively, the normalization coefficients are directly computed as normalization factors.

In act 68, the line-of-response events are normalized. The measurements from the CBM PET scan are normalized to account for efficiency variation. Each line-of-response is normalized by a corresponding normalization coefficient. The same normalization coefficient may be used for different events corresponding to the same virtual line-of-response. Different virtual line-of-response events are normalized by different CBM normalization coefficients. Alternatively, different normalization coefficients are determined for different line-of-response events, even if part of the same virtual line-of-response.

To normalize, the line-of-response events are weighted by the CBM efficiency. The line-of-response measure is multiplied by the inverse of the normalization coefficient. Each line-of-response event is weighted by a corresponding one of the normalization coefficients for a given detector pair or group of detectors.

In act 70, the object space is reconstructed from the output of the normalizing. The line-of-event data, after normalization, is used in reconstruction.

Any reconstruction may be used. In one embodiment, the reconstruction is a Poisson iterative reconstruction. OSEM, FORE, or other reconstructions may be used. The reconstruction estimates the object or patient space from the lines-of-response. The detected events are used to iteratively determine using forward, backward, or forward and backward projection.

An image is reconstructed by reconstructing the object space and then rendering or imaging from the reconstructed object. The image is of the patient, such as PET image showing function or uptake of the radiopharmaceutical. The image benefits from the normalization by avoiding variance due to differences in detection efficiency for different lines-of-response.

The reconstruction accounts for the continuous bed motion. Chunking may be used in the reconstruction. Clinical reconstruction requirements (e.g. image should be available after acquisition with smallest possible delay) may lead to reconstruction of the continuous bed motion sinogram in parts or "chunks." Any reconstructed part (chunk) size may be used. Large overlapping of chunks may not lead to loss in counts, but redundancy in reconstruction. Chunk size may be increased at the expense of reconstruction delay after scanning. In one embodiment, the chunk size and chunk overlap are chosen to match S&S acquisition. In alternative embodiments, chunking is not used.

There is no change in scatter correction in transition from S&S to CBM. Scatter is estimated for each chunk. While scatter estimation suffers from unknown activity outside the field of view, scatter scaling is performed to overcome this problem. Scaling in principle should be the same procedure for CBM acquisition. Nevertheless, more uniform axial scatter estimation may result in CBM as compared to S&S. This result is likely due to fact that scatter scaling is performed on segment zero data only, where S&S acquisition demonstrated axial non-uniformity.

Figure 5B:
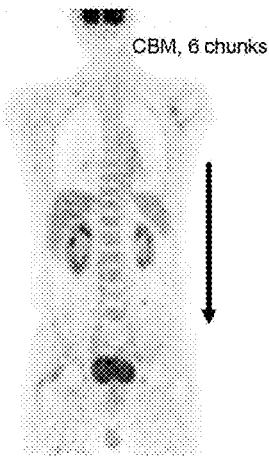
FIGS. 5B and 5C are medical images reconstructed using CBM and S&S, respectively.
Figure 5C:
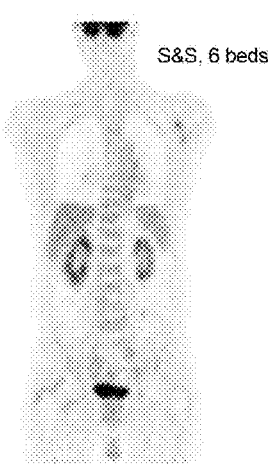
Figure 5D:
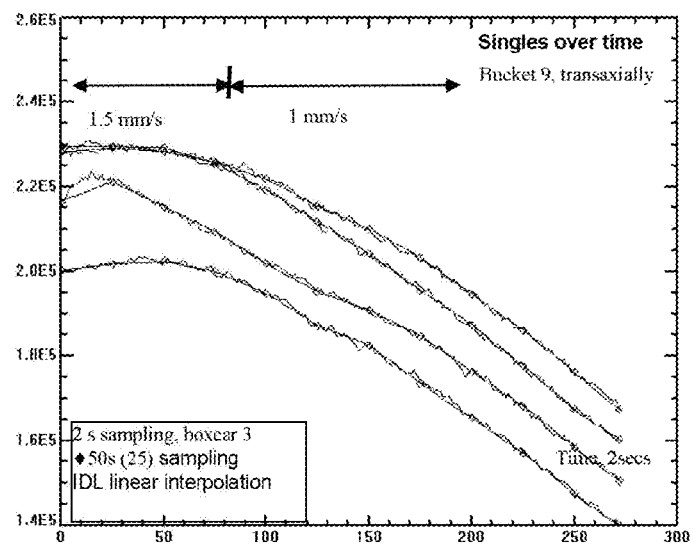
FIG. 5D shows example singles as a function of time.

FIG. 5B shows an example reconstructed image using CBM reconstruction after normalization with CBM normalization coefficients. Variable speed acquisition is performed, with 1.5 mm/s for the chest region and 1.0 mm/s for the abdominal region, as represented in FIG. 5D. The movement direction is shown by the arrow such that the head region is acquired first. Six "chunks" are used for the CBM reconstruction, but other numbers may be used. FIG. 5C shows an example of reconstruction using S&S reconstruction of the same patient. A comparison shows that uniformity of CBM patient reconstruction is achieved, even though bed velocity is changed during acquisition. The images look similar except physiological changes due to a 30 minute delay between acquisitions.

FIG. 5A shows a CBM object plane sensitivity profile 32. The CBM object plane sensitivity profile 32 was obtained by single slice rebinning (SSRB) of corresponding inverse CBM normalization coefficients. The CBM profile 32 is a combination of sensitivities for each chunk. This profile demonstrates the effect of variable bed speed as well as isotope decay. The S&S profile 30 is shown for comparison.

The reconstructed volumes may be output for storage. Alternatively, one or more images of the reconstructed volume are displayed. Any functional, anatomical, or functional and anatomical imaging may be used. Cross sections of the volume may be mapped to display values. The volumes may be rendered, such as using surface or projection rendering, from one or more viewing directions.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for computing normalization coefficients in continuous bed motion acquisition, the method comprising:
   acquiring, with a positron emission tomography (PET) scanner having a plurality of rings of detectors, line-of-response events from radioactive decay of an isotope in a patient while the patient is moving on a bed at different velocities in the PET scanner;
   calculating normalization coefficients for the line-of-response events, the normalization coefficients calculated to represent efficiencies for pairs of the detectors, the calculating being a function of a decay correction efficiency for the isotope and step sizes that vary as a function of time in response to the different velocities of the bed;
   normalizing the line-of-response events as a function of the normalization coefficients; and
   reconstructing an image of the patient with an output of the normalizing, wherein calculating comprises calculating over time with the step size, $\Delta t$, where contribution at a particular time t is:

$$(e^{-\lambda t}\Delta t)/(n^{scanner}(s(t))),$$

where $\lambda \Delta t$ is less than 1, $\lambda$ is a decay correction constant, t is time, $e^{-\lambda t}$ is the decay correction efficiency, s(t) is an empirical global singles rate of the PET scanner, and $n^{scanner}$ is a scanner efficiency.

2. The method of claim 1 wherein acquiring comprises acquiring with the moving comprising continuous bed motion.

3. The method of claim 1 wherein calculating the normalization coefficients comprises calculating with the step sizes being specific to the acquiring for the patient, such that different combinations of step sizes result for different patients.

4. The method of claim 1 wherein calculating comprises calculating with the step sizes comprising each step size being change in time given by a change in axial position divided by a velocity for the axial position.

5. The method of claim 1 wherein calculating comprises calculating as a function of the decay correction efficiency with the decay correction efficiency comprising a decay correction constant for the isotope.

6. The method of claim 1 wherein calculating comprises calculating the normalization coefficients for each line-of-response at different positions relative to the PET scanner due to the motion of the patient.

7. The method of claim 1 wherein normalizing comprises weighting the line-of-response events by inverses of the normalization coefficients, each line-of-response events weighted by a corresponding one of the normalization coefficients for the given pair of the detectors.

8. The method of claim 4 wherein calculating comprises calculating with the change in axial position comprising the motion of the patient from one line-of-response position to another line-of-response position of the PET scanner.

9. The method of claim 5 wherein calculating comprises calculating with the decay correction efficiency being an exponential factor that is a function of time.

* * * * *